United States Patent [19]
Malmqvist et al.

[11] Patent Number: 5,492,840
[45] Date of Patent: Feb. 20, 1996

[54] SURFACE PLASMON RESONANCE SENSOR UNIT AND ITS USE IN BIOSENSOR SYSTEMS

[75] Inventors: Magnus Malmqvist; Robert Karlsson; Inger Rönnberg, all of Upsala, Sweden

[73] Assignee: Pharmacia Biosensor AB, Upsala, Sweden

[21] Appl. No.: 681,544

[22] PCT Filed: Nov. 9, 1989

[86] PCT No.: PCT/SE89/00643

§ 371 Date: May 10, 1991

§ 102(e) Date: May 10, 1991

[87] PCT Pub. No.: WO90/05305

PCT Pub. Date: May 17, 1990

[30] Foreign Application Priority Data

Nov. 10, 1988 [SE] Sweden .................. 8804074

[51] Int. Cl.⁶ .................. G01N 33/543; G01N 33/551; G01N 33/553
[52] U.S. Cl. .................. 436/518; 356/317; 356/318; 356/445; 385/12; 422/82.05; 422/82.11; 435/808; 436/164; 436/524; 436/525; 436/527; 436/528; 436/529; 436/530; 436/531; 436/805; 436/819
[58] Field of Search .................. 436/518, 524, 436/525, 805, 808, 819, 527, 528, 529, 530, 531, 164; 422/58, 61, 82.05, 82.11; 356/317, 318, 445; 385/12; 435/808; 530/412, 413, 417

[56] References Cited

U.S. PATENT DOCUMENTS

| | | | |
|---|---|---|---|
| 4,444,878 | 4/1984 | Paulus | 436/518 |
| 4,737,453 | 4/1988 | Primus | 435/5 |
| 4,978,50-3 | 12/1990 | Shanks et al. | 422/82.11 |
| 4,992,385 | 2/1991 | Godfrey | 422/57 |

FOREIGN PATENT DOCUMENTS

| | | |
|---|---|---|
| 0112721 | 7/1984 | European Pat. Off. . |
| 0184600 | 6/1986 | European Pat. Off. . |
| 0202021 | 11/1986 | European Pat. Off. . |
| 0226470 | 6/1987 | European Pat. Off. . |
| 0254575 | 1/1988 | European Pat. Off. . |
| 0276142 | 7/1988 | European Pat. Off. . |
| 0276968 | 8/1988 | European Pat. Off. . |
| 0286195 | 12/1988 | European Pat. Off. . |
| WO84/04171 | 10/1984 | WIPO . |
| WO85/04811 | 11/1985 | WIPO . |

OTHER PUBLICATIONS

Suresh et al, Proc. Natl. Acad. Sci. USA, vol. 83, pp. 7989–7993 (1986).
Brennan et al, Science, vol. 229, pp. 81–83 (1985).

*Primary Examiner*—David Saunders
*Assistant Examiner*—Christopher L. Chin

[57] ABSTRACT

Methods for functionalizing sensing surfaces to be used in systems for measuring simultaneously several properties of one biomolecule as well as for simultaneously measuring the concentrations of a plurality of biomolecules in a sample. The invention furthermore also relates to sensor units containing such surfaces, to the use thereof for surface characterization of biomolecules, and to a reagent kit for functionalization of sensing surfaces.

23 Claims, 6 Drawing Sheets

SURFACE PLASMON RESONANCE SENSOR UNIT AND ITS USE IN BIOSENSOR SYSTEMS

BACKGROUND OF THE INVENTION

1. Field of the Invention

The present invention relates to the field of biosensors and is more specifically concerned with methods for functionalizing sensing surfaces to be used in systems for measuring simultaneously several properties of one biomolecule, as well as measuring simultaneously the concentrations of a plurality of biomolecules in a sample. The invention furthermore also relates to sensor units containing such surfaces, a reagent kit for functionalizing the surfaces, and to the use thereof in the context of surface characterization of biomolecules.

2. Description of Related Art

According to Aizawa (1983) a biosensor is defined as being a unique combination of a receptor for molecular recognition, for example a selective layer with immobilized antibodies, and a transducer for transmitting the values measured. One group of such biosensors will detect the change which is caused in the optical properties of a surface layer due to the interaction of the receptor with the surrounding medium. Among such techniques may be mentioned especially ellipso-metry and surface plasmon resonance. In order for these types of techniques to work satisfactorily in actual practice, certain requirements have to be fulfilled—i.e., the requirement that the sensing surface employed can easily be derivatized so that it will then contain the desired receptor; and moreover that said surface will not produce any nonspecific binding, i.e., binding of components other than those that are intended, or that such binding in cases where it does occur will not furnish any significant contribution to the measuring signal. Some prior art in this field is exemplified below.

EP-A2-276 968 discloses a biograting for use in a light immunoassay comprising a polysilicon or single crystalline silicon surface having a biological diffraction grating design of an active binding reagent, such as an antibody, an antigen, a hapten, protein A, a lectin, biotin and avidin.

EP-A1-276 142 discloses a method of improving the sensitivity of assays based upon surface plasmon resonance by increasing the optical thickness of the optical surface, utilizing an additional complex forming reagent.

EP-A2-112 721 discloses an assay technique based upon observing the changes in the optical properties of a pre-formed surface, such as a grating, capable of binding the species to be assayed, the sample being applied to the surface by smearing. The pre-formed surface, such as a profiled plastic strip, may have a plurality of zones, each of which is coated with a different receptive material.

EP-A1-184 600 discloses a method for determining species dissolved in a liquid analyte by the use of an optical waveguide carrying a light signal and having one or more coatings of reactants specific to the species to be analyzed.

In somewhat simplified terms, the technique of surface plasmon resonance—by abbreviation SPR, as derived from the initials surface plasmon resonance—may be said to be a technique in which changes in the refractive index in a layer close to a thin free-electron metal film are detected by consequential changes in the intensity of a reflected p-polarized light beam (see for example Raether, H (1977)).

Thus, in this case, the sensing surface is a metal film with receptors or ligands as they will be called henceforth, these being generally molecules or molecular structures which interact selectively/specifically with one or more biomolecules.

The metal film is applied on a medium of a type that is suitable for the measuring method employed. In the case of SPR, this means that a transparent dielectric material, e.g., in the form of a glass plate, is used for directing a beam of light to the metal surface.

As regards the use of SPR procedures, most of the publications that have come forth up to now describe laboratory equipment for singular measurements. Although such a laboratory arrangement is apt to convey a general idea as to the potential of the method, all this is still a far cry from a commercially satisfactory instrument.

Most of the work done has focused on various methods for binding a particular biomolecule to the metal surface. In the first publication indicating the possibilities of SPR technology in biochemical analyses, Liedberg, B. et al (1983) have first adsorbed a monolayer of IgG onto a silver surface, and then adsorbed to said monolayer a layer of anti-IgG, in order to then study the effect in respect to the resultant change in the resonance angle. Others too, e.g., Cullen, D. C. et al. (1987/88), have utilized adsorption of biomolecules directly to a metal surface when studying immune complex formation in the IgG/anti-IgG system using the SPR technique with a gold-coated diffraction grating. EP 257955 describes a method according to which the metal film is coated with silica and optionally treated with a silanizing reagent; and in EP 202021, the metal film has been coated with an organic layer that may contain, for example, antibodies directed against a specific antigen and optionally bound by covalent bonds. According to EP 254575, an optical structure of the type such as is suitable for, e.g., SPR applications, may be produced by coating the metal film with a layer of an organic polymer, by means of the so-called "solvent casting technique". In a preferred embodiment, cellulose nitrate is employed, and a number of well-known methods are mentioned for binding bioselective ligands to the layer.

In other respects, the actual instrumentation equipment is described in only very brief terms, comprising an arrangement with a light source from which plane-polarized light in its plane of incidence is reflected from the metal surface and then intercepted by a detector, the output signal of which is usually recorded as a function of the angle of incidence. In this case, the metal film has been applied directly to a prism (see, e.g. Daniels, P. B. et al (1988)) or on a glass substrate, as a rule in the form of a microscope slide which is arranged in optical contact with the prism via immersion oil having a suitable refractive index (see, for example, GB 2197068). A variant form has been described by Webb et al. in EP 257955 according to which the glass substrate has been provided with a series of triangular projections from which rays of light from a lens system are coupled to the metal surface and then, after reflection, out to the detector system. In some cases it has been indicated that sample solutions are contacted with the sensing surface in a flow cell; but no actual practical directions are given as to how this is done.

SUMMARY OF THE INVENTION

However, a commercially useful biosensor system must fulfil at least the following minimum requirements:

The system has to contain a replaceable sensor unit consisting of a substrate of a dielectric material, for example a glass substrate, which has one of its faces coated with a metal film containing one sensing surface or preferably a plurality of sensing surfaces. Such sensing surfaces have to be functionalized for selective interaction with the desired biomolecules. The most versatile construction, which thus represents the optimum choice, contains two or more sensing surfaces that have been functionalized in situ with the desired ligand.

The system has to contain a block unit for liquid handling, with conduit means for conveying the reagent solution and sample solution over each respective sensing surface, either parallelly, in that the liquid flow is subdivided into minor streamlets, or with the sensing surfaces arranged in series, so that they will be flushed one after the other with the same body of liquid.

The system has to contain an optical instrumentation unit adapted to direct incident beams of light to each of the sensing surfaces on the metal film and to detect the reflected radiation from the various metal film regions corresponding to each respective one of the sensing surfaces.

An evaluation unit is required which converts the detector signal after calibration to a parameter that is proportional to the amount of substance on the sensing surface. This in turn may be proportional to the association/dissociation rate constant, diffusion constant, affinity, concentration of molecules in solution, etc.

Such a system is described in greater detail in our copending PCT-application entitled "Optical biosensor system" (based upon Swedish patent application No. 8804075-3), the disclosure of which is incorporated by reference herein.

Basically, the sensor unit forming the subject matter of the present application is a construct of the type as shown in FIG. 1, where (1) is the dielectric substrate and (2) is the metal film, the sensing surfaces thereof being designated symbols $m_n$, where n is an integer greater than 0. In the FIG. 1 example, three such sensing surfaces designated $m_1$ to $m_3$ are shown, but the concept of this construct does not put any limit on the number of sensing surfaces. Similarly, of course, the geometrical shape of the substrate may be a different one, e.g., a square or circular shape, and with a variety of thicknesses.

The unit is intended to be brought into optical communication with the optical unit by means of a medium having suitable optical properties, for instance an immersion oil having a refractive index such as to minimize reflection losses at the interfaces. It is advantageous however, to employ a transparent elastic material, such as a suitable silicone rubber, having a matching refractive index, because this will eliminate the necessity of handling oils which have to be wiped off every time a sensor unit is replaced. It is desirable to couple the sensor unit to the optical system with the aid of a so-called "optointerface" (see the aforesaid PCT-application), consisting of a thin glass plate having both of its faces coated with the transparent elastic material, e.g., in the form of strings of square cross section. With this arrangement, air inclusions are avoided when the optointerface is mounted in contacting position with the optical unit and sensor unit, respectively. Each string, of course, has a projection area covering the corresponding sensing surface. Preferably each elastic material piece forms a coating all over its underlying surface but has thickened portions at the positions of each of the corresponding sensing surfaces. To facilitate handling, the glass plate with its elastic material pieces thereon may suitably be mounted in a holder.

Moreover, the sensor unit should be coupled to the block unit for liquid handling in such a manner that reagent and sample solutions in flow cells are caused to pass over the sensing surfaces $m_n$ either in series or in parallel.

The sensor unit is made in one piece, for example, from a glass plate that has been coated with a thin film of a metal which is acceptable in technical SPR procedures, preferably silver or gold, the coating having been applied by means of, e.g., a so-called sputtering process. To the metal film has been attached a layer of an organic polymer or a hydrogel forming a so-called basal surface which may contain functional groups for binding the desired ligands. This is described in more detail in our copending PCT-application entitled "Sensing surfaces capable of selective biomolecular interactions to be used in biosensor systems" (based upon Swedish patent application No. 8804073-8), the disclosure of which is incorporated by reference herein.

When measurements are to be carried out, the sensing surfaces have to be functionalized with different ligands capable of interaction with biomolecules. As regards the manner in which such surfaces are produced, there are several routes available: The basal surface may be provided with the desired biospecific ligands already when it is being manufactured, i.e., in the factory; but a system offering much more versatile applicabilities is obtained if the basal surface is provided in situ with, in each case, that particular ligand in which the user is interested. If the sensing surfaces of the sensor unit are arranged in series in the path of liquid flow emanating from the liquid handling block unit, then these sensing surfaces should each contain their own particular functional group, $f_1$ to $f_n$, for coupling to ligands $L_l$ to $L_m$.

The ligands employed by the user are in this case bi- or polyfunctional. Every ligand contains an anti-f function which is utilized for immobilization on the corresponding sensing surface, plus one or more bioselective functions for interaction with biomolecules in the sample solution.

In a system having three sensing surfaces arranged in series in the flow path of sample solution, the ligands may be, for example, antif$_1$-L$_1$ and antif$_2$-L$_2$ and antif$_3$-L$_3$. Via f$_1$, the first ligand binds to the first surface by way of interaction between $f_1$ and antif$_1$, whereby the binding ligand $L_1$ becomes exposed on that surface. Similarly, the second surface is functionalized with $L_2$ via binding to $f_2$ etc. This will thus require a series of reagents, antif$_n$-L$_m$, where antif$_n$ is employed for immobilization of the reagent and $L_m$ is exposed on the surface for interaction with biomolecules in solution.

In cases where the system uses parallel surfaces, all of the sensing surfaces may be equal when they are mounted in the system, because every reagent solution is made to pass over only one sensing surface. The sensing surface contains a function that is activated for binding the particular ligand in question.

The functions which are generally useful in processes according to the present invention are such as are well known from liquid chromatography processes. Some examples are: hydroxyl, carboxyl, amino, aldehyde, hydrazide, carbonyl or vinyl groups. The reactions occurring when these or other groups are used for coupling various types of ligands are well known from the literature.

In a preferred embodiment a hydrogel is bound to the metal surface, e.g., via a disulfide. The hydrogel may be, for example, a polysaccharide such as, e.g., agarose, dextran, carrageenan, alginic acid, starch, cellulose or derivatives, thereof such as, for instance, carboxymethyl derivatives or a water-swellable organic polymer such as, e.g., polyvinyl alcohol, polyacrylic acid, polyacrylamide and polyethylene glycol.

Highly suitable in this context are, especially, polysaccharides of the dextran type, which are noncrystalline in nature, in contrast to, for instance, cellulose. For chromatograph purposes, dextran has been used to a very great extent as the matrix for binding biomolecules; and one of the merits of the present concept is that this entire technical field is now available also for biosensor applications, viz. for the final step involving immobilization of the appropriate ligand.

In an embodiment which is apt to further illustrate the invention, the dextran matrix is then activated for binding ligands according to a known technique, for example, in conformity with any one of the following procedures:

A hydrazide function is generated in the dextran matrix for binding ligands containing aldehyde groups, e.g., antibodies in which the carbohydrate chain has been oxidized so as to contain an aldehyde function. In this case, the dextran matrix is at first modified with carboxymethyl groups, part of which are reacted to form hydrazide groups. With this activated matrix, at least two important advantages are obtained: (1) The matrix still contains unreacted carboxyl groups, which at low ionic strengths will function as ion exchangers; and by electrostatic interaction, the ligand to be attached to the dextran matrix is concentrated. (2) The ligand concentrated to the surface is efficiently bound to the matrix by means of condensation of ligand aldehyde groups with the hydrazide function of the matrix.

According to another embodiment, a portion of the carboxyl groups present in carboxymethyl modified dextran are modified to form reactive ester functions, for example, by treatment with an aqueous solution of N-hydroxysuccinimide and N-(dimethylaminopropyl)-N'-ethylcarbodiimide hydrochloride. In the same way as in the first embodiment, the residual charges, id est unreacted carboxyl groups, contribute to achieving a concentration of ligands to the surface. Then as a next step, ligands containing amine groups, e.g., proteins and peptides, can be bound covalently to the dextran matrix.

According to an alternative procedure, the aforesaid reactive ester is used for reaction with a disulfide-containing compound such as, for example, 2-pyridyl-2'-aminoethyl disulfide; this will result in the formation of a matrix containing disulfide groups that can be employed for coupling of thiol- or disulfide-containing ligands such as, e.g., reduced F(ab) fragments of immunoglobulins.

To sum up, there are a very large number of ligands which may be used for the detection of biomolecules by interaction therewith. As will be readily appreciated, ion exchanger groups, metal chelating groups, and various types of receptors for biological molecules such as are known from conventional liquid chromatography may be employed for constructing suitable systems even in complex measuring milieus.

DETAILED DESCRIPTION OF THE INVENTION

In one embodiment, so-called chimeric molecules (bi- or polyfunctional molecules) are employed for functionalizing the sensing surfaces. The chimeric molecules comprise one portion binding to the basal surface, e.g., the aforesaid dextran-coated sensing surface, and one portion having an affinity for the biomolecule to be detected. Bi- or polyfunctional molecules for use according to the invention may be produced in a variety of ways, e.g., by means of chemical coupling of the appropriate molecules or molecule fragments, by means of hybridoma techniques for producing bifunctional antibodies, or by means of recombinant DNA techniques. This last-mentioned technique involves the fusing of gene sequences coding for the structures which are wanted in the product, this product then being expressed in a suitable expression system such as, e.g., a culture of bacteria. Chemical coupling of biomolecules or fragments thereof can be performed in accordance with one of the coupling methods that have been developed for the immobilization of biomolecules. A suitable reagent is, e.g., SPDP N-succinimidyl 3-(2-pyridylthio)propionate, a heterobifunctional reagent (from Pharmacia AB, Sweden, and with a coupling technique as described by Carlsson et al (1978)). In the case of dextran, the chimeric molecule may consist of an antibody against dextran conjugated with a biospecific ligand, e.g., an immunoglobulin. With a series of such chimeric molecules which thus contain a dextran antibody and a group of a different specificity, a so-called measuring cassette containing a plurality of identical sensing surfaces in one instrument can easily be subjected to parallel activations for the purpose of detecting a plurality of biomolecules. According to an alternative procedure, a sensing surface is modified with a so-called hapten for binding chimeric molecules to the surface. Thus, for example, a reactive ester surface as described above may be derivatized with a theophylline analog which is then utilized for binding chimeric molecules. In this case, the chimeric molecule consists of an antibody against theophylline conjugated with a biospecific ligand. These embodiments very clearly reveal the great versatility attainable with the use of surfaces according to the present invention, in as much as it is so easy for the user to provide the same single basal surface with the desired ligand (receptor). Proteins vary inter se in respect of their stability to environments that tend to reverse biospecific bonds. With the aid of chimeric molecules, the desired degree of reversibility can be obtained due to haptens being chemically more stable than the biospecific pair which is to be studied.

Figure 1:
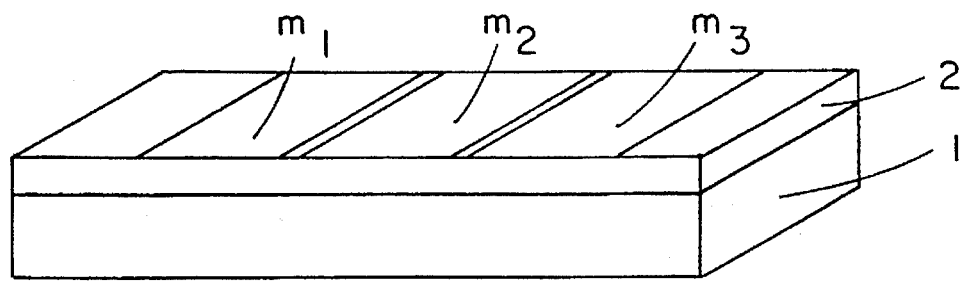
FIG. 1 shows the construction of the sensor unit of the present invention, wherein (1) is a dielectric substrate and (2) is a metal film, and wherein $m_1$, $m_2$, and $m_3$ represent sensing surfaces. The geometrical shape of the substrate may be different, for example, square or circular, and the substrate can have a variety of thicknesses.
Figure 2:
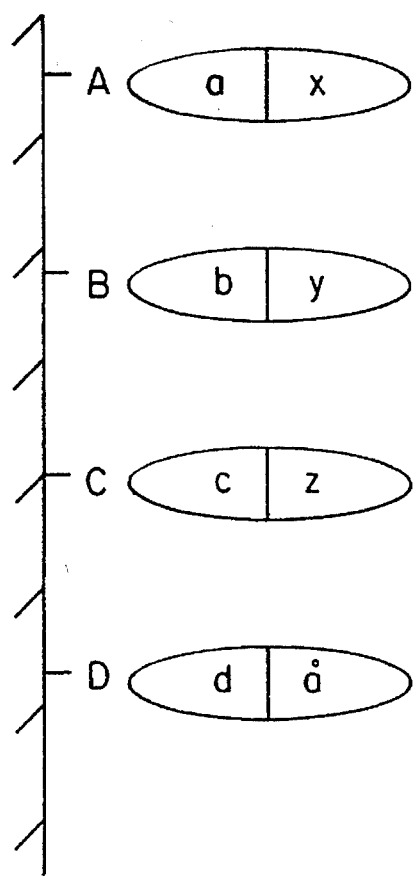
FIG. 2 is a schematic illustration of an embodiment of the present invention wherein chimeric molecules (bi- or polyfunctional molecules) are employed for functionalizing the sensing surfaces. Four different chimeric molecules, a-x, b-y, c-z, and d-å, are shown attached to four different functional groups, A, B, C, and D, respectively, on a sensing surface by reversible bonds, a—A, b—B, c—C, and d—D, respectively.

FIG. 2 gives a schematical illustration of the above mentioned embodiment with chimeric molecules as functionalizing agents. In the figure, four different chimeric molecules are shown, a-x, b-y, c-z, d-å, attached to four different functional groups, A, B, C and D, respectively, on a respective sensing surface by reversible bonds, a—A, b—B, c—C and d—D, respectively. If the analytical system handles the analyses in parallel a protein binding to, e.g., A can be used for all the channels and utilized in chimeric contructions with x, y, z etc.

Examples of surface binding structures of the chimeric molecule (a, b, c, d) are auxin-binding protein (Tellmann, U et al. (1989)) or an antibody, while the analyte binding structure (x, y, z, å) may be exemplified by Ab/Fab, streptavidin or protein G, or cloned parts of these molecules. (Lorrick J. W. et al. (1989) and Ward E. S. et al. (1989)).

The functional groups A, B, C, D are here preferably relatively small molecules which are covalently bound to the surface and which are stable, such that the biospecific bonds between these molecules and the respective chimeric molecules may be broken down by, e.g., HCl, NaOH or additives such as miscible organic solvents without the molecules A–D being destroyed, thereby permitting the surface to be regenerated. As examples of such small molecules may be mentioned theophylline, steroid hormones and thyroxine, which may be regenerated by sodium hydroxide and additives. Many proteins can also withstand extreme conditions, but normally proteins are less stable. Some antibodies may also be reversed in spite of high binding strength.

As mentioned above this system has considerable flexibility due to the possibility of providing a number of different chimeric molecules binding to a measuring basic surface functionalized with, e.g., A, i.e., the chimeric molecules have one and the same surface binding structure, in this case a, while the analyte binding structure hereof varies. One and the same measuring basic surface may in such manner easily be functionalized with respect to several different analytes. An analogous manner, corresponding chimeric molecules may, of course, be prepared, which will bind to the groups B, C and D, respectively. The need for one or more basic systems for chimeric molecules depends, of course, inter alia on whether a serial or parallel liquid handling system is used.

Proteins as a base for chimeric molecules (i.e., the surface binding structure thereof) must have strong bonds to their low-molecular chemically stable partners on the measuring basic surface. Also, no part thereof should, of course, be capable of interacting with the biosystems to be analyzed. Thus, e.g., clinical systems may have a biospecific pair from the vegetable kingdom, while vegetable samples may have a unique animal pair as the base.

Preferably, the analytical system is such that the binding of the chimeric molecule to the analyte may be reversed under conditions differing from those permitting the binding between the measuring surface and the chimeric molecule to be broken. In such manner, depending on the conditions, the sensing surface may be regenerated at two different levels, i.e., either for binding a new analyte, or for refunctionalizing the surface with the same or other chimeric molecules.

The above-described system based upon chimeric molecules may, of course, be used for measurements with only a single sensing surface or area as well as with two or more such areas. The system may also not only be used for SPR techniques, but for all methods based upon measuring the change of physical or chemical properties of a surface caused by ligand interactions therewith, such as all internal reflectance based methods, photoacoustic methods, piezoelectric methods, surface acoustic wave (SAW) methods, etc. In a further aspect, the invention therefore provides a reagent kit comprising the above chimeric molecules for use in such methods. Such a kit may optionally include one or more sensing surface members.

The invention thus relates to a replaceable sensor unit which is to be used in biosensor systems based on the surface plasmon resonance technique and containing at least an optical block unit for irradiating a metal film and detecting light rays reflected by said film, plus a liquid handling block unit for transporting reagents or sample solutions to sensing surfaces on the metal. Each sensing surface contains at least one functional group, and the surfaces are to be arranged in series or parallel in the path of liquid coming from the liquid handling block unit. Particularly, the invention is concerned with sensor units in which these sensing surfaces differ inter se in having different functional groups or ligands for interaction with biomolecules present in the sample. The invention moreover relates to processes for further functionalization of these sensing surfaces by binding to them bi- or polyfunctional ligands which will interact with biomolecules in the sample when the measuring operation is taking place.

The invention also comprises a method for surface characterization of biomolecules, in that sample molecules are made to pass over a combination of sensing surfaces, each of which carries at least one unique ligand. The degree of interaction with each of the ligands will then provide information about the surface structure of the biomolecules. Also, by real time measurement, one will then at the same time obtain information on kinetic parameters. Such combinations of sensing surfaces may, for example, contain ligands such as types of, ion exchanger groups, hydrophobic/hydrophilic groups, metal ion chelating groups, groups showing different degrees of bioselectivity or biospecificity, etc. Moreover the structure of a bound biomolecule can be studied by subjecting the sensing surface to flows of reagent solutions containing molecules that will bind to different structural elements on the target molecule which is being studied. Examples of such reagent molecules are monoclonal antibodies against various epitopes. Over each surface sequential injection of ligands may be performed, and the interaction with surface bound molecules can be analyzed in relation to earlier structural knowledge about the biomolecule of interest, or a bi- or polyfunctional ligand can be the base for the next ligand.

I. Derivatization of basal surface, i.e., sensing surface, with bound dextran thereon I.1 Synthesis of hydrazide surface Bromoacetic acid, 3.5 g, was dissolved in 27 g of 2M sodium hydroxide solution. The mixture was poured over a dextran-treated surface and incubated for 16 hours at 25° C. in a shaker incubator. The surface was washed with water, whereupon the aforesaid procedure was repeated once.

After washing, the surface was treated for 5 minutes with 0.8 g of N-(dimethylaminopropyl)-N'-ethylcarbodiimide hydrochloride (EDC) in 20 ml of water, this being then followed by an addition of 4.0 ml of hydrazine hydroxide in 20 ml of water. The surface was incubated for 16 hours in a shaker incubator at 25° C. and then washed with water.

I.2 Synthesis of surface with reactive ester function

N-hydroxysuccinimide, 0.69 g, and EDC, 1.15 g, were dissolved in 30 ml of water. The mixture was poured over a carboxy-methyl-modified dextran surface according to I.1 and incubated for 60 minutes at 25° C. in a shaker incubator. The surface was washed with water.

I.'Synthesis of theophylline surface

A solution of 5 mM 8-(3-aminopropyl)-theophylline (R. C. Boguslaski et al (1980) in 0.1M carbonate buffer, pH 8.0, was incubated with an N-hydroxysuccinimide ester activated dextran surface (according to Example I.2) overnight at 25° C., whereupon the surface was washed with water.

II. Coupling of ligand to derivatized basal surfaces

II.1 Anti-IgE antibody

Anti-IgE antibody (Pharmacia Diagnostics AB, Sweden) in 10 mM acetate buffer, pH 5.5, was oxidized for 20 minutes with 10 mM sodium periodate on an ice bath according to the method described by O'Shannessey (1985). After replacement of the buffer, the antibody was coupled to the hydrazide-modified dextran surface (Example I.1) in 10 mM acetate buffer, pH 4.0. Unbound antibody was eluted with 0.1M glycine, pH 2.5.

II.2 Antibeta-2-microglobulin antibody

Antibeta-2-microglobulin antibody (Pharmacia Diagnostics AB, Sweden) was oxidized and coupled as in Example II.1 to the hydrazide-modified dextran surface.

II.3 Rabbit-antimouse light chain antibody (RAMLC)

RAMLC antibody in 10 mM acetate buffer, pH 5.5 (Pharmacia Diagnostics AB, Sweden) was coupled during a 20 min. period to an N-hydroxy-succinimide ester derivatized dextran surface (according to Example I.2) whereupon unbound antibody was removed by rinsing the surface in PBS buffer, pH 7.4, and in 0.1M glycine, pH 2.5.

III. Biomolecule assaying by means of SPR technique

The sensing surface was mounted in an SPR measurement device comprising a flow cell; after adjustment of the optical instrumentation, the measuring signal was studied as a function of time under constant flow conditions.

III.1 Assays for determining concentration and subclass identification of monoclonal antibodies After covalent immobilization of RAMLC antibodies to the sensing surface (Example II.3), culture medium containing monoclonal antibodies was injected.

Figure 3:
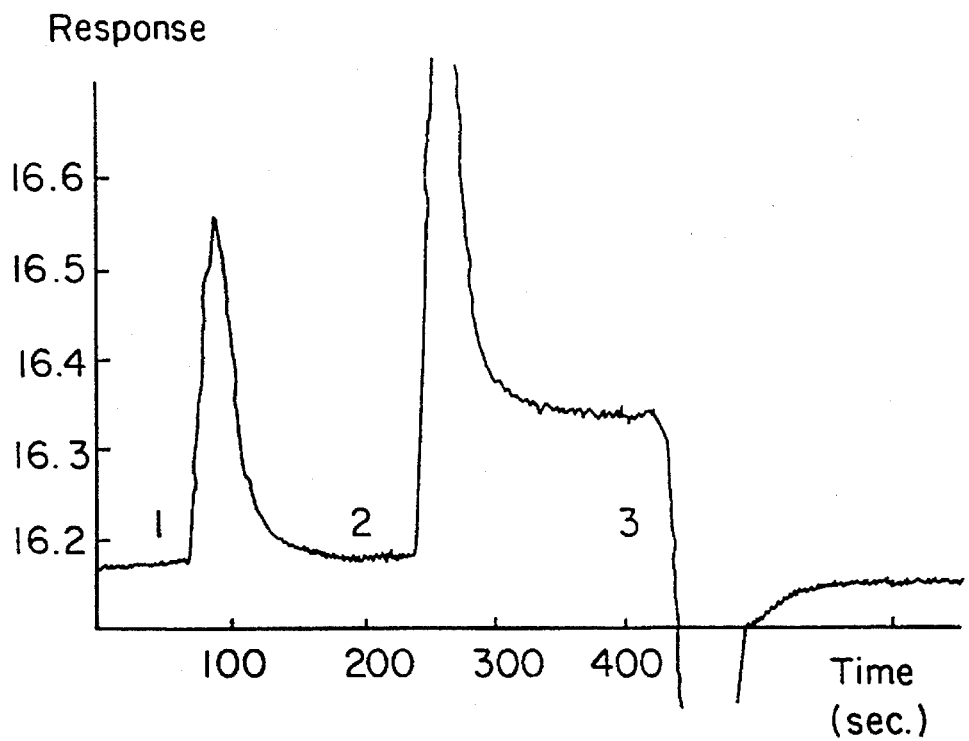
FIG. 3 shows the response curve for (1) injection of culture medium, (2) injection of culture medium containing monoclonal antibody, and (3) regeneration with 0.1M glycine, pH 2.5, in Example III.1.

FIG. 3 shows the response curve for (1) injection of culture medium, (2) injection of culture medium containing monoclonal antibody, and (3) regeneration with 0.1M glycine, pH 2.5.

Figure 4:
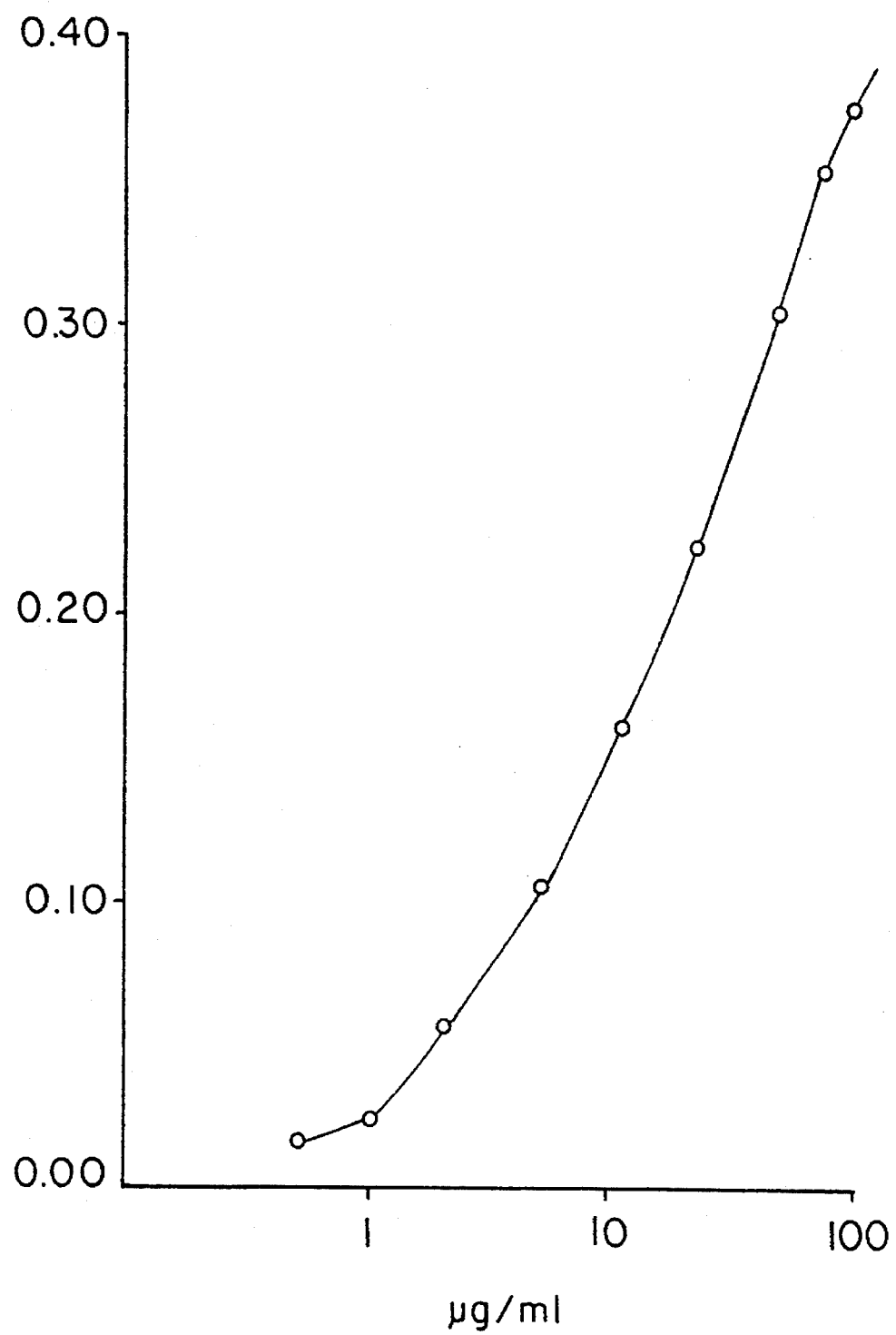
FIG. 4 shows the standard curve for different concentrations of a monoclonal IgG1 antibody in Example III.1. The dose-response curve has an accuracy better than ±10% in the range of from 5 to 100 μg antibody/ml.

FIG. 4 shows the standard curve for different concentrations of a monoclonal IgG1 antibody. The dose-response curve has an accuracy better than ±10% in the range of from 5 to 100 µg antibody/ml.

Figure 5:
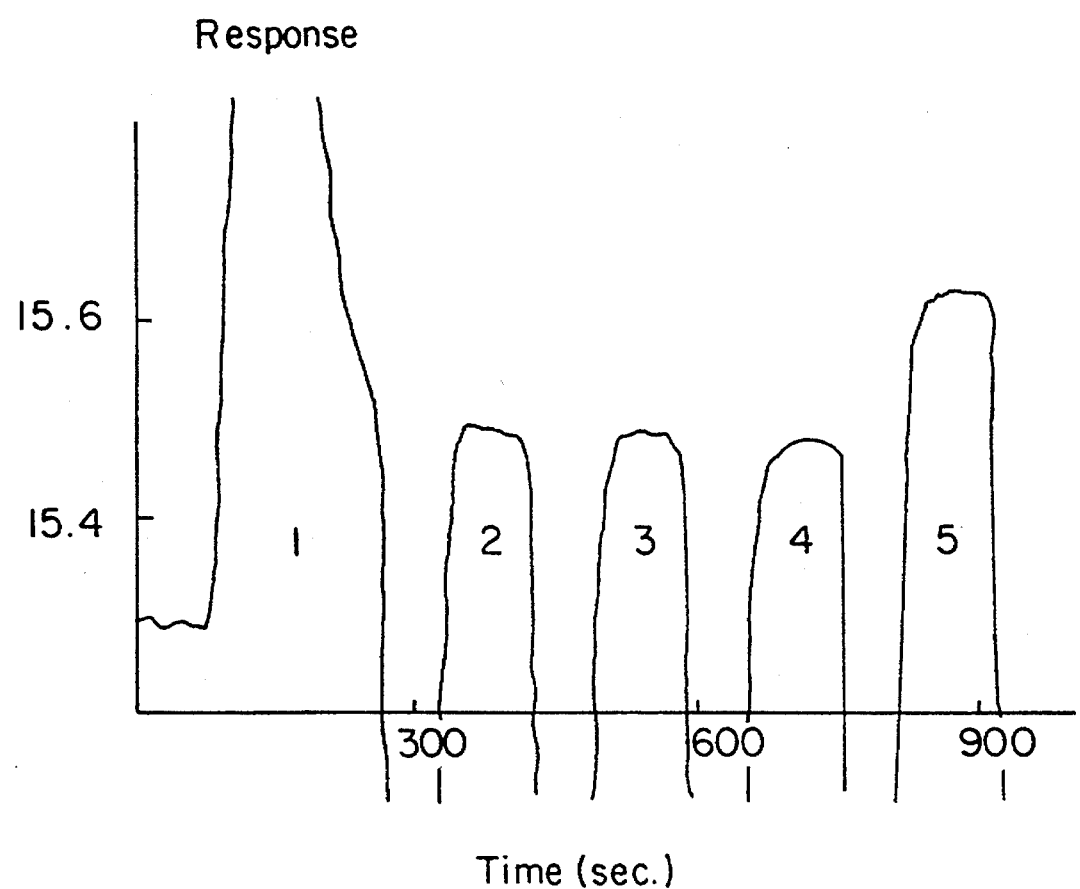
FIG. 5 shows sequential injections of subclass-specific reagents and identification of the bound monoclonal as an IgG1 antibody in Example III.1: (1) Monoclonal antibody binds to the surface, and thereafter follows injection of (2) anti-IgG2a, (3) anti-IgG3, (4) anti-IgG2b, and (5) anti-IgG1 (which binds to the surface).

FIG. 5 shows sequential injections of subclass-specific reagents and identification of the bound monoclonal as an IgG1 antibody: (1) Monoclonal antibody binds to the surface, and thereafter follows injection of (2) anti-IgG2a, (3) anti-IgG3, (4) anti-IgG2b, and (5) anti-IgG1 (which binds to the surface). In order to verify the reversibility and repeatability of the system, the antibody binding and subclass identification have been repeated 100 times on the same single surface.

III.2 Studies of affinity and kinetics with anti-theophylline conjugates as carriers of sensor molecules Protein A and protein C were introduced on a theophylline surface in the form of conjugates with an anti-theophylline antibody (chimeric molecules). The interaction between protein A or protein G respectively and monoclonal antibodies of different subclasses could be studied in this manner.

Preparing conjugates

Monoclonal anti-theophylline antibody No. 459, monoclonal antibodies of different IgG subclasses, monoclonal anti-IgE antibodies of IgG1 subclass No E164, 95 and 121, and IgE were obtained from Pharmacia Diagnostics AB, Sweden. The anti-theophylline antibody was digested with pepsin to form F(ab)'-2 fragments or was employed as the intact antibody. Protein A, protein G and SPDP were obtained from Pharmacia LKB Biotechnology AB, Sweden.

Protein A—anti-theophylline conjugate was prepared by means of SPDP modification of the two molecules according to a method described by Carlsson et al (1978). After reduction of modified protein A with 10 mM DTE a mixture was prepared of 3.8 mg anti-theophylline of modification degree 1.8 (pyridyl disulfide groups per molecule) and 13.8 mg reduced protein A of modification degree 1.3 (thiols/molecule).

Conjugation was allowed to proceed overnight in 0.1M phosphate buffer with 0.1M sodium chloride at pH 7.7. Conjugates of protein G and the F(ab)'-2 fragments of anti-theophylline were prepared in an analogous manner.

Analysis

Measuring surfaces with bound theophylline lend themselves readily to functionalization with the above described conjugates; and with two parallel sensing surfaces—one functionalized with the protein A conjugate and the other one functionalized with the protein G conjugate—it was possible to very quickly compare the affinities of protein A and protein G, respectively, for a series of immunoglobulins. The results obtained confirmed the differences in this respect as reported by, e.g., Gusset et al (1986).

The experiment demonstrates not only the possibilities of quickly obtaining qualitative results in kinetics and affinity measuring operations but also the versatility of a sensing surface according to this invention, in view of the fact that such a sensing surface, when used with the appropriate reagents, can be made to serve for a very wide range of different types of assays.

Since the protein A/G interactions are reversible at pH 2.5 while the anti-theophylline-theophylline binding is stable in character the immunoglobulins binding to protein A/G are easily replaceable. At a high pH, for example 75 mM NaOH, the chimeric molecule can also be replaced on the sensing surface; this is apt to still further demonstrate the versatility of the method.

III.3 Beta-2-microglobulin determination with a so-called sandwich procedure

Measurement of beta-2-microglobulin (Pharmacia Diagnostics AB, Sweden) was carried out with a sensing surface containing antibeta-2-microglobulin antibodies according to Example II.2. The measuring signal for beta-2-microglobulin binding to the sensing surface was recorded as a function of the concentration thereof in solution, both directly (primary response) and after signal enhancement with a secondary immunosorbent-purified antibody which binds to the surface via the primarily bound beta-2-microglobulin and forms a so-called sandwich structure (secondary response). An at least 10 times lower detection level is obtained due to this readily conceivable and experimentally simple process.

IV. Derivatization of sensing surfaces in a biosensor system

A sensor unit containing 4 sensing surfaces, all of them equal and carrying carboxymethyl dextran, was introduced into a biosensor system via an optointerface, whereupon one surface was derivatized with aminotheo-phylline and another with aminobiotin. Reagent solutions containing the conjugates anti-theophylline-transferrin and antibiotin-albumin were injected, thus binding to each respective one of the surfaces. Binding of antibodies directed against albumin and transferrin respectively, was then demonstrated due to binding of these components from a sample solution.

IV.1 Coupling of ligand

The flow of an acetate buffer (0.2M, pH 5.5) was directed to two of the channels, and the carboxymethyl dextran was activated during 10 minutes by injecting into each channel 50 μl of a mixture of 0.2M EDC and 0.5M NHS (see Example I.2). Into each of these channels were then injected 50 μl of a solution which contained aminotheophylline (1 mg/ml), or aminobiotin (1 mg/ml) respectively, in 0.1M NaHCO$_3$, pH 8.8, and the coupling reaction was allowed to proceed for 5 minutes. Thereafter the surfaces were washed with two salt pulses—buffers as above, but in 1.0M NaCl.

IV.2 Preparing antibody conjugates

F(ab')2 fragments of anti-theophylline, antibiotin, albumin and transferrin were modified with SPDP as described in Example III.2, and after reduction of modified albumin and transferrin, the conjugates were prepared by means of mixing the F(ab')2 fragment of anti-theophylline with reduced transferrin, and treating antibiotin with reduced albumin. The conjugation reaction was allowed to proceed overnight in an 0.1M phosphate buffer (0.1M NaCl, pH 7.7).

Figure 6:
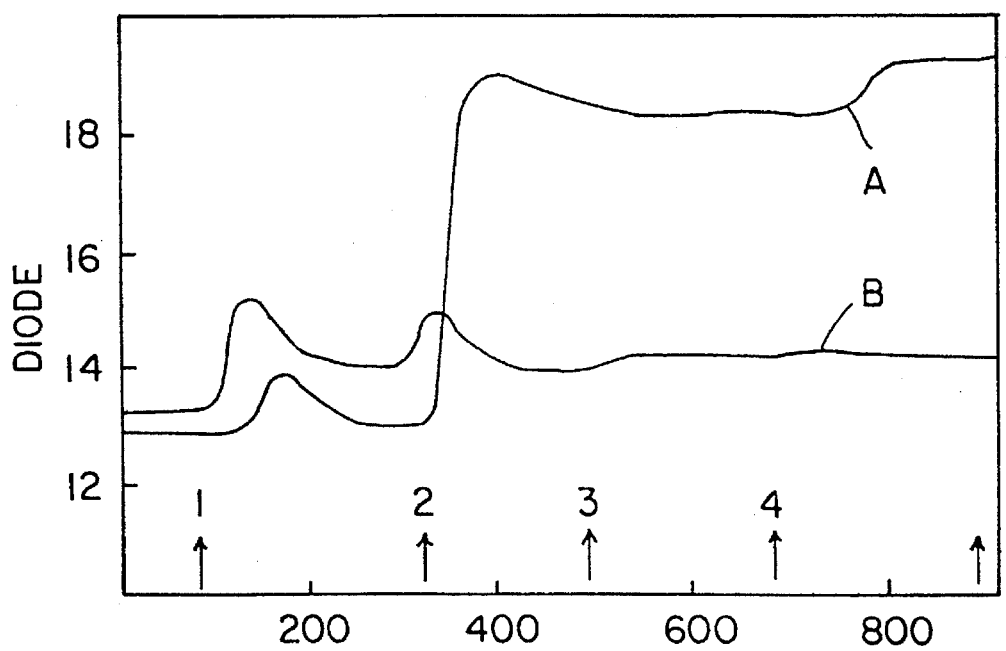
FIG. 6 shows sequential injections of the respective conjugates plus test substances (antialbumin and antitransferrin) in Example IV.2. Curve A represents the response to antitheophyllin-transferrin, and curve B represents the response to antibiotin-albumin. The numbered arrows indicate the respective injections: (1) antibiotin-albumin; (2) antitheophyllin-transferrin; (3) antialbumin; and (4) antitransferrin. The surfaces were completely regenerable with sodium hydroxide, and could be used in a series of experiments.

The channels were then coupled in series with the aid of the block unit for liquid handling, and sample solutions were injected which contained the conjugates individually, as well as mixtures thereof. Measuring results showed that the conjugates bound to only that surface which exposed the "correct" functional group; that is, anti-theophylline-transferrin bound to the theophylline surface and antibiotin-albumin bound to the biotin surface. These respective surfaces thus possess ligands for the antitransferrin and, respectively, the antialbumin; this was confirmed when sample solutions were injected which contained those antibodies. FIG. 6 shows sequential injections of the respective conjugates plus test substances (antialbumin and antitransferrin). Curve A represents the response to antitheophylline-transferrin, and curve B that to antibiotin-albumin. The numbered arrows indicate the respective injections: (1) antibiotin-albumin, (2) antitheophylline-transferrin, (3) anti-albumin, (4) antitransferrin. The surfaces were completely regenerable with sodium hydroxide and could be used in a series of experiments.

V. Studies concerning the binding structures of a protein, so-called epitope mapping The HIV p24 protein has attracted much interest since the presence of either the protein itself or antibodies directed against it is considered to be the first indication of a HIV infection.

Figure 7A:
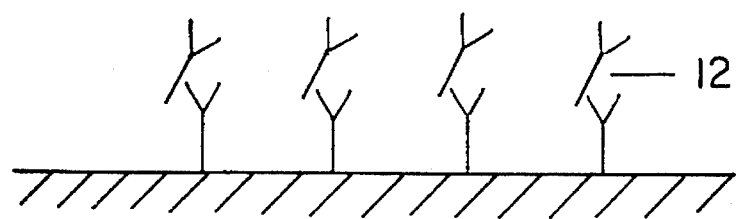
FIG. 7(a) shows a sensing surface with bound rabbit-antimouse-Fc via which the monoclonal (12) is immobilized in Example V. Monoclonal (12) in turn binds p24 from a reagent solution.
Figure 7B:
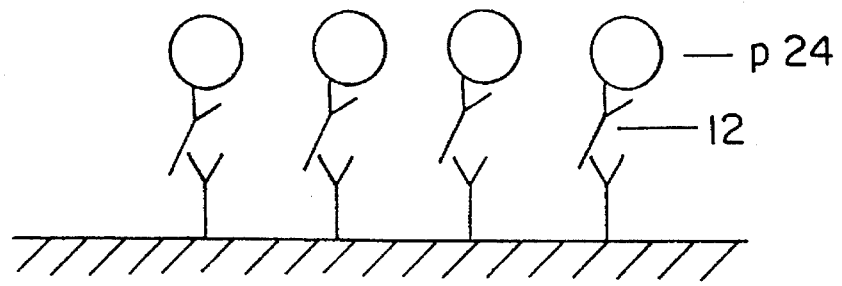
FIG. 7(b) shows the system of FIG. 7(a) ready for analysis of the interaction with the remaining monoclonals, i.e., the monoclonals other than (12), which is used for immobilizing p24.

When test systems are constructed it is important that one should know a plurality of independent binding sites on the protein. A series of antibodies against p24 was therefore analyzed with biosensor systems containing biosensor units according to the invention. Fifty-four culture media containing anti-p24 monoclonals were analyzed, the procedure employed here comprised (i) immobilization of one of the monoclonals (12) by binding to rabbit-antimouse-Fc that had been bound covalently to a dextran-hydrazide surface according to Example 1, followed by (ii) biospecifically binding p24 to the surface, this p24 then being employed as the ligand for binding the other monoclonals. The method is illustrated schematically in FIGS. 7(a)–7(b). FIG. 7(a) shows a sensing surface with bound rabbit-anti-mouse-Fc via which the monoclonal (12) is immobilized. Monoclonal (12) in turn binds p24 from a reagent solution, and in FIG. 7(b) the system is ready for analysis of the interaction with the remaining monoclonals, i.e., the monoclonals other than (12) which latter is being used for immobilizing p24.

In a first series of analyses, the binding of each monoclonal was studied separately. The results showed thirty-one of them to bind, i.e., they did not utilize the same binding domain as (12).

The positive media were analyzed further in various different combinations; the injections for this purpose were made sequentially. This procedure provides a direct answer as to whether or not a previously bound monoclonal will block binding site accessibility for a succeeding monoclonal.

Figure 8A:
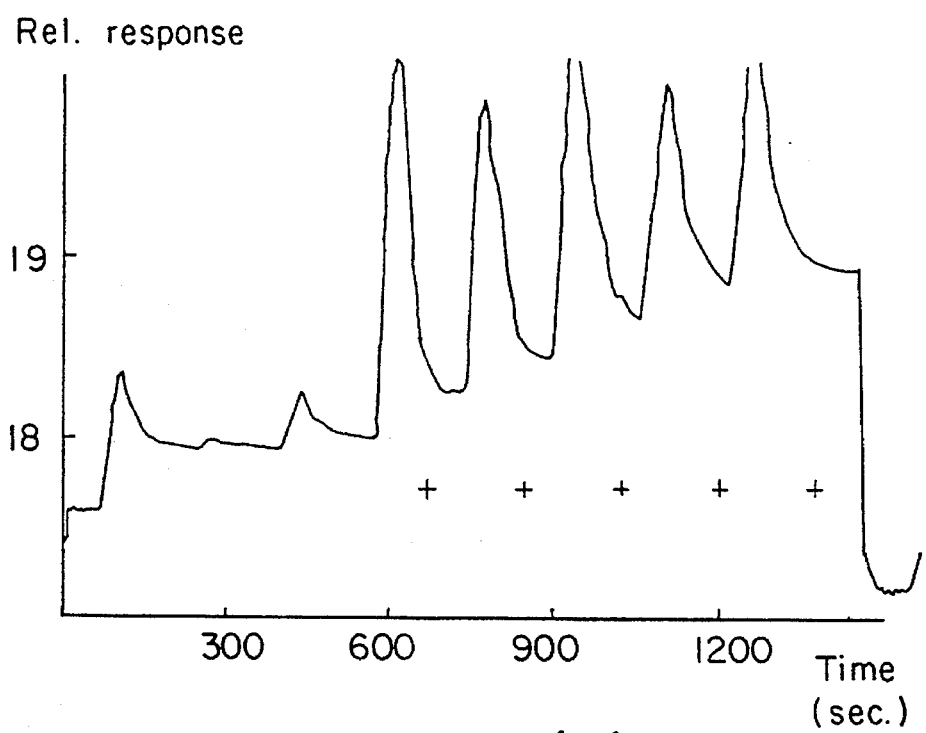
FIG. 8(a) shows the response of the detector in the experiment described in Example V, wherein the positive media were analyzed in various different combinations. Five monoclonals were injected sequentially, and all bind irrespective of the fact that a monoclonal had been bound earlier.
Figure 8B:
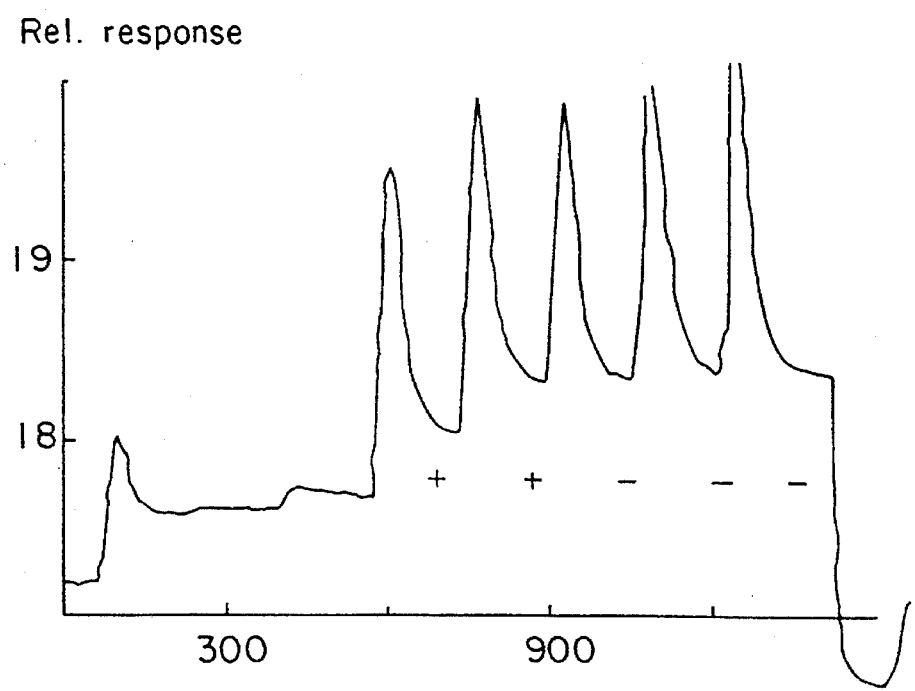
FIG. 8(b) shows the response of the detector in the experiment described in Example V, wherein the positive meida were analyzed in various different combinations. Five monoclonals were injected sequentially. The first and second monoclonals are seen to bind (+), while for the remaining three monoclonals, the remaining binding sites are blocked (−).

FIGS. 8(a) and 8(b) show the response of the detector in such an experiment. Five monoclonals have been injected sequentially, and all of them are seen to bind, irrespective of the fact that a monoclonal has been bound earlier. In (b), the first and second monoclonals are found to bind (+) while for the remaining three monoclonals, the remaining binding sites are blocked (−).

By a systematic investigation of a number of combinations of monoclonals, six principal domains have been identified which contain independent binding sites; these binding sites may thus be utilized for specific and independent binding of groups of monoclonals on the p24 molecule.

By way of this series of experiments it has thus been demonstrated inter alia that monoclonals (22), (43), (28), (2), (1), (33), (17) and (34) bind to independent domains, so these will thus be of interest for further evaluation in the context of the construction of a testing method.

References

Aizawa, M (1988), Anal. Chem. Symp. 17: 683.
Boguslaski, R. C. et al (1980), Immonuassays: Clinical Laboratory Techniques for the 1980s, Ed. Nakamura, R. M., Dito W. R. & Tucker III, E. S.; ARL. New York 1980, 45–64.
Carlsson et al (1978), Blochem J 173: 723.
Cullen, D. C. et al (1987/88), Biosensors 3: 211–225.
Daniels, P. B. et al (1988), Sensors and Actuators 15: 11–18.
Guss, B. et al (1986 ), The EMBO Journal 5(7): 1567–1575.

Liedberg, B. et al (1983), Sensors and Actuators 4: 299–304.
Lorrick, J. W. et al (1989, Biotechnology 7: 934–938.
O'Shannessy (1985), J Appl Blochem 7: 347.
Raether, H. (1977), Physics of Thin Films, Ed. Hass, G., Francombe, M. and Hoffman, R., Academic Press, New York, 145–261.
Tellmann, U. et al (1989), The EMBO Journal 8 (9): 2463–2467.
Ward, E. S. et al (1989), Nature 341: 544–546.

We claim:

1. A sensor unit for use in a biosensor system based on surface plasmon resonance technology, comprising:
   a dielectric substrate which is replaceable in said biosensor system and which is coated with a metal film, said film having two or more sensing areas arranged so as to be passed in series or in parallel by a liquid stream,
   each of said sensing areas comprising a layer of an organic polymer or hydrogel over said metal film, containing at least one functional group supporting bi- or polyfunctional molecules capable of specific binding with biomolecules present in said liquid stream which are to be detected, said bi- or polyfunctional molecules comprising ligands that can specifically bind to biomolecules in a sample and a functional structure which can form reversible bonds with said at least one functional group which, through said functional structure, are coupled to said sensing area by a reversible bond, such that said two or more sensing areas can be regenerated for refunctionalization with the same or other bi- or polyfunctional molecules, wherein
   coupling between said bi- or polyfunctional molecules and said biomolecules in said liquid stream is selectively reversible such that the bi- or polyfunctional molecule-functionalized sensing areas can be regenerated, permitting repeated use of the functionalized sensor unit.

2. The sensor unit of claim 1, wherein said bi- or polyfunctional molecules are selected from a group of chimeric molecules having an identical sensing area binding structure, but having varying analyte binding structures.

3. The sensor unit of claim 1, wherein said metal film is a film of silver or gold.

4. The sensor unit of claim 1, wherein said sensing areas contain at least one functional group selected from the group consisting of hydroxyl, carboxyl, amino, aldehyde, hydrazide, carbonyl, and vinyl.

5. The sensor unit of claim 1, wherein a hydrogel is bound to said metal film via disulfide bonds.

6. The sensor unit of claim 1, wherein said hydrogel is a polysaccharide or a water-swellable organic polymer.

7. The sensor unit of claim 6 wherein said water-swellable organic polymer is selected from the group consisting of polyvinyl alcohol, polyacrylic acid, polyacrylamide, and polyethylene glycol.

8. The sensor unit of claim 6, wherein said polysaccharide is selected from the group consisting of agarose, dextran, carrageenan, alginic acid, starch, cellulose, and a derivative of any one of the foregoing.

9. The sensor unit of claim 8, wherein said derivative is a carboxymethyl derivative.

10. The sensor unit of claim 8, wherein said polysaccharide is dextran.

11. The sensor unit of claim 10, wherein said dextran is activated for binding said ligand or ligands by generating at least one member selected from the group consisting of carboxymethyl, carboxyl, hydrazide, ester, and disulfide groups therein.

12. The sensor unit of claim 11, wherein said ester groups are derivatized with a hapten.

13. The sensor unit of claim 12, wherein said hapten is theophylline.

14. The sensor unit of claim 1, wherein said functional group is selected from the group consisting of ion exchanger groups, metal chelating groups, and receptors for biological molecules.

15. The sensor unit of claim 1, wherein said metal film is coated with a layer of dextran.

16. The sensor unit of claim 15, wherein said chimeric molecules are antibodies against dextran conjugated with a biospecific ligand.

17. The sensor unit of claim 16, wherein said biospecific ligand is an immunoglobulin.

18. The sensor unit of claim 1, wherein said functional group is a molecule selected from the group consisting of theophylline, a steroid hormone, and thyroxine.

19. The sensor unit of claim 1, wherein said bi- or polyfunctional molecules contain a function for immobilizing said bi- or polyfunctional molecules on the corresponding sensing area, which function is common to all sensing areas, plus one or more analyte binding structures for interacting with biomolecules in said liquid stream, wherein said analyte binding structures vary between said sensing areas.

20. A method for detecting binding sites on a biomolecule, comprising:
    contacting a sample with said sensing areas of claim 1, and
    detecting any binding interacting between said biomolecule and said sensing areas, indicating the presence of a corresponding binding site on said biomolecule.

21. The method of claim 20, which further comprises providing a plurality of sensing areas, each having its own specific ligand, and serially or in parallel contacting a sample solution containing said biomolecule with said sensing areas in order to detect binding sites on said biomolecule.

22. A process for functionalizing said sensing areas of the sensor unit according to claim 1, comprising:
    introducing said sensor unit into a biosensor system based on surface plasmon technology which comprises a liquid handling block unit for conveying sample solutions to said sensing areas, and
    distributing by means of said liquid handling block unit a flow of a reagent solution containing a bi- or polyfunctional molecule to each of said sensing areas so that said bi- or polyfunctional molecule reversibly binds to said at least one functional group of said sensing areas, said bi- or polyfunctional molecule including (i) a functional group that binds to said sensing areas to immobilize said bi- or polyfunctional molecule on said sensing areas and (ii) at least one additional functional group that possesses specific binding affinity for a target molecule and which is exposed on each of said sensing areas for interaction with said target molecule.

23. The process of claim 22, wherein each of said sensing areas containing a unique functional group is arranged in series in said flow containing a bi- or polyfunctional ligand for each respective area.

* * * * *